(12) United States Patent
Kwak

(10) Patent No.: US 7,655,044 B2
(45) Date of Patent: Feb. 2, 2010

(54) ARTIFICIAL FACET JOINT DEVICE HAVING A COMPRESSION SPRING

(75) Inventor: Seungkyu Daniel Kwak, Grafton, MA (US)

(73) Assignee: Depuy Spine, Inc., Raynham, MA (US)

(*) Notice: Subject to any disclaimer, the term of this patent is extended or adjusted under 35 U.S.C. 154(b) by 679 days.

(21) Appl. No.: 11/011,330

(22) Filed: Dec. 13, 2004

(65) Prior Publication Data

US 2006/0129239 A1 Jun. 15, 2006

(51) Int. Cl.
*A61F 2/44* (2006.01)
(52) U.S. Cl. .................................. 623/17.13
(58) Field of Classification Search ............ 606/61, 606/69–71; 623/17.11–17.16
See application file for complete search history.

(56) References Cited

U.S. PATENT DOCUMENTS

| | | | |
|---|---|---|---|
| 4,759,469 A * | 7/1988 | Lowrance et al. .............. 221/75 |
| 5,092,866 A | 3/1992 | Breard et al. | |
| 5,401,269 A * | 3/1995 | Buttner-Janz et al. .... 623/17.15 |
| 5,571,191 A | 11/1996 | Fitz | |
| 5,603,713 A * | 2/1997 | Aust et al. .................. 606/279 |
| RE36,758 E | 6/2000 | Fitz | |
| 6,132,464 A | 10/2000 | Martin | |
| 6,235,059 B1 * | 5/2001 | Benezech et al. ......... 623/17.16 |
| 6,440,169 B1 * | 8/2002 | Elberg et al. .............. 623/17.16 |
| 7,060,100 B2 * | 6/2006 | Ferree et al. .............. 623/17.16 |
| 7,238,204 B2 * | 7/2007 | Le Couedic et al. ...... 623/17.11 |
| 7,261,739 B2 * | 8/2007 | Ralph et al. .............. 623/17.13 |
| 7,377,942 B2 * | 5/2008 | Berry ....................... 623/17.11 |
| 2003/0004572 A1 | 1/2003 | Goble | |
| 2003/0028250 A1 * | 2/2003 | Reiley et al. ............. 623/17.11 |
| 2004/0002708 A1 * | 1/2004 | Ritland ........................ 606/61 |
| 2004/0111154 A1 * | 6/2004 | Reiley ..................... 623/17.11 |
| 2005/0119748 A1 * | 6/2005 | Reiley et al. ............. 623/17.11 |
| 2006/0149383 A1 * | 7/2006 | Arnin et al. .............. 623/17.13 |
| 2006/0235535 A1 * | 10/2006 | Ferree et al. ............. 623/17.16 |

FOREIGN PATENT DOCUMENTS

| | | | |
|---|---|---|---|
| EP | 1330987 A1 * | 7/2003 |
| FR | 2774581 A1 * | 8/1999 |
| WO | WO 00/53126 | 9/2000 |
| WO | WO 0203882 A3 * | 1/2002 |

OTHER PUBLICATIONS

Gardner et al., Graf Ligamentoplasty: a 7-year Follow-Up, Eur Spine J, 2002, pp. S157-S163, vol. 11, Supp. 2, Springer-Verlag.
Senegas, Mechanical Supplementation by No-Rigid Fixation in Degenerative Intervertebral Lumbar Segments: The Wallis System, Eur Spine J, 2002, pp. 164-169, vol. 11, Supp. 2, Springer-Verlag.

* cited by examiner

*Primary Examiner*—Thomas C Barrett
*Assistant Examiner*—Nicholas Woodall

(57) ABSTRACT

A prosthetic facet joint having compression springs interposed between articulating surfaces for providing gradual resistance to extreme movements.

9 Claims, 16 Drawing Sheets

ARTIFICIAL FACET JOINT DEVICE HAVING A COMPRESSION SPRING

BACKGROUND OF THE INVENTION

One of the most common surgical interventions in spine today is arthrodesis, or spine fusion, in which two or more adjacent vertebral bodies are fused together in order to alleviate pain associated with the disc(s) located between those vertebral bodies. Approximately 300,000 such procedures are performed annually in the United States alone. Clinical success varies considerably, depending upon technique and indications, and consideration must be given to the concomitant risks and complications.

While spine fusion generally helps to eliminate certain types of pain, it has also been shown to decrease function by limiting the range of motion for patients in flexion, extension, rotation and lateral bending. Furthermore, it is believed that spine fusion creates increased stresses on (and, therefore, accelerated degeneration of) adjacent non-fused motion segments. Additionally, pseudoarthrosis, resulting from an incomplete or ineffective fusion, may reduce or even totally eliminate the desired pain relief for the patient. Also, the fusion device(s) used to effect fusion, whether artificial or biological, may migrate out of the fusion site, thereby creating significant new problems for the patient. Lastly, the recuperation time after a fusion procedure can be lengthy.

Recently, several attempts have been made to recreate the natural biomechanics of the spine through the use of an artificial disc. Artificial discs are intended to restore articulation between vertebral bodies so as to recreate the full range of motion normally allowed by the elastic properties of the natural disc, which directly connects two opposed vertebral bodies. However, the artificial discs developed to date do not fully address the mechanics of motion of the spinal column.

In addition to the foregoing, posterior elements called the facet (or zygapophyseal) joints help to support axial, torsional and shear loads that act on the spinal column. Furthermore, the facet joints are diarthroidal joints that provide both sliding articulation and load transmission features. The facet's articular surfaces contact in extension, limiting extension and increasing compressive load. The articular surfaces also contact on one side of the spine in lateral bending and axial rotation, also limiting rotation and transferring load.

However, the facet joints can also be a significant source of spinal disorders and, in many cases, debilitating pain. The articular cartilaginous surfaces can degenerate due to mechanical or biological factors and cause pain as with other joint osteoarthritis, or enlarge and produce stenosis. For example, a patient may suffer from arthritic facet joints, severe facet joint tropism or otherwise deformed facet joints, facet joint injuries, etc. There is currently a lack of suitable intervention procedures for facet joint disorders. Facetectomy, or the removal of the facet joints, may provide some relief, but is also believed to significantly decrease the stiffness of the spinal column (i.e., hypermobility) in all planes of motion: flexion and extension, lateral bending, and rotation. Furthermore, problems with the facet joints can also complicate treatments associated with other portions of the spine. By way of example, contraindications for artificial discs include arthritic facet joints, absent facet joints, severe facet joint tropism or otherwise deformed facet joints. Accordingly, there is a need for a facet joint replacement that addresses these concerns.

U.S. Pat. No. Re. 36,758 (Fitz I) discloses an artificial facet joint where the inferior facet, the mating superior facet, or both, are simply covered with a cap. Because placement of the cap requires no preparation of the bone or articular surfaces; it covers and, therefore, preserves the bony and articular structures.

However, simple capping of the facet has several potential disadvantages. If the facet joint is osteoarthritic, a cap will not remove the source of the pain. Additionally, at least in the case of surface replacements for osteoarthritic femoral heads, the capping of articular bone ends has proven to lead to clinical failure due to mechanical loosening. This clinical failure is hypothesized to be a consequence of disrupting the periosteum and ligamentum teres femoris, both of which play a role in delivering nutrition to the femoral head, thereby leading to avascular necrosis of the bony support structure for the surface replacement. It is possible that corresponding problems could develop from capping the facet. Another potential disadvantage of facet capping is that in order to accommodate the wide variability in anatomical morphology of the facets, not only between individuals but also between levels within the spinal column, as well as due to associated hypertrophic and degenerative changes, a very wide range of cap sizes and shapes is required, or significant reshaping.

U.S. Pat. No. 6,132,464 ("Martin") describes a replacement of the articular surfaces and means for supporting and fixing these replacements to the posterior processes. The articulating surface itself is described as having "the shape, position, and orientation of a natural articular facet". It discloses a spinal facet joint prosthesis that is supported on the lamina (which is sometimes also referred to as the posterior arch). Extending from this support structure are inferior and/or superior blades that replace the cartilage at the facet joint. The prosthesis of U.S. Pat. No. 6,132,464 generally preserves existing bony structures and therefore does not address pathologies which affect the bone of the facets in addition to affecting the associated cartilage. Furthermore, the prosthesis of U.S. Pat. No. 6,132,464 requires a secure mating between the prosthesis and the lamina. However, the lamina is a very complex and highly variable anatomical surface. As a result, in practice, it is very difficult to design a prosthesis that provides reproducible positioning against the lamina so as to correctly locate the cartilage-replacing blades for the facet joints.

The U.S. Pat. No. 6,132,464 patent describes articular surfaces and means of attachment, but does not describe a capsular replacement.

U.S. Pat. No. 5,571,191 ("Fitz II") describes a facet prosthesis comprising superior and inferior components, pyramidal or conical in shape, fitting over the facet processes, and having low friction mating surfaces. Although this patent describes articular surfaces and means of attachment, it does not describe a capsular replacement.

Gardner et al. *Eur. Spine J* (2002) (Supp 2): S157-163, discloses Graf ligamentoplasty as a means of stabilizing and reducing mobility of one or more severely symptomatic motion segments associated with degenerative disc disease. FIG. 1 shows Polyester bands wrapped around a pair of pedicle screws extending from adjacent vertebral bodies. This ligament also appears to be disclosed in U.S. Pat. No. 5,092,866 ("Breard"). According to Gardner, appropriate Graf bands immobilizes the motion segment in lordosis with the facet joints in a position of full extension, in which position they are very stable. See page S159. Accordingly, Graf ligamentoplasty essentially immobilizes the facet joint. Gardner does not disclose a mobile ligament that traverses a facet joint.

Senegas et al., *Eur. Spine J.* (2002) 11 (Supp 2): S164-9 discloses a Wallis implant system comprising a titanium interspinous blocker and a Dacron ligament, wherein the blocker is placed between two spinous processes and the Dacron ligament wraps around spinous processes. See p. S165. Accordingly, Senegas does not disclose a ligament that traverses a facet joint.

WIPO PCT Published Patent Application No. WO 00/53126 ("Ogun") discloses a memory metal implant for fixing an articulated joint, including a facet joint.

The Dynesys system is generally used as a replacement for the natural posterior longitudinal ligament. The system includes a cable housed inside a plastic sheath, and is attached to superior and inferior pedicles. The ligament of the Dynesys system does not traverse a facet joint.

US Published Patent Application No. 2003/0004572 ("Goble") discloses a prosthesis comprising an intervertebral disc prosthesis and a fact joint prosthesis. Goble does not disclose a facet joint ligament. FIG. 12 of Goble discloses a facet joint replacement system wherein each of the superior and inferior components are fixed respectively to the upper and lower pedicles. However, the superior component of the Goble system has no adjustability (i.e., the screw-articulation surface distance is fixed). Second, the articulation surface appears to be set higher than the pedicle screw securing the inferior component. In such a case, long term bearing may cause twirling of the inferior component about the lower pedicle screw axis.

As demonstrated above, it is the goal of an artificial facet joint to recreate the physiological biomechanics of a normal spine to the extent possible. These physiological mechanics include a non-linear relationship between force and displacement. During the initial motion of the facet joint, termed the "neutral zone", the stiffness of the joint is low. As motion progresses, and the joint enters the "elastic zone", the stiffness of the joint increases. The ligamentous and fibrous structures around the spine create this behaviour, as more fibers become taught as motion increases.

It has been found that the non-linear force-displacement behaviour found in a physiologic facet joint is difficult to reproduce using artifical ligaments, as large strain (5 -30%) is required in the face of large forces. In general, artificial ligaments do nor possess both high ultimate strength and high ultimate strain. Therefore, most artificial ligaments have difficulty replicating large natural movements.

Accordingly, there is a need to provide the natural non-linear force displacement relationship of a facet joint without the need of ligamentous prosthetic components.

SUMMARY OF THE INVENTION

The present invention has been developed that provides the natural non-linear force displacement relationship of a facet joint by using compression spring elements.

In one preferred embodiment, the device has two concave links. The upper link attaches to the top vertebra and the lower link attaches to the lower vertebra. The left and right arms of each concave link articulate to guide flexion and extension while resisting anterior shear. Three compressive springs made of a rubber-like material (such as polyurethane) are associated with the upper and lower links. One compressive spring is centrally located within the links while the other two springs are located outside of and on either side of the linkage. As the spine goes into flexion, the central compression spring is loaded. When the spine goes into extension, the outer compression springs are loaded.

By appropriately selecting both the location wherein the springs are loaded and the stiffness of the springs, the desired non-linear force-displacement relationship of the facet joint can be obtained.

The device also allows some lateral bending motion, but ultimately limits the motion as one of the outside springs is loaded. Finally, the rotation of the spine is severely limited as the upper and lower links cross each other preventing translation in the medial-lateral direction.

Therefore, in accordance with the present invention, there is provided a prosthetic facet joint device comprising:
  a) a first component adapted for fixation to a first vertebra comprising:
    i) a first side, and
    ii) a second side facing away from the first side, and
  b) a second component adapted for fixation to a second vertebra comprising:
    i) a first side, and
    ii) a second side facing away from the first side, wherein the first side of the first component opposes the first side of the second component at a first location to form a first interface, and wherein the second side of the first component opposes the second side of the second component at a second location to form a second interface, and
  c) a first compression resistance means associated with the first interface, and
  d) a second compression resistance means associated with the second interface.

DESCRIPTION OF THE FIGURES

FIG. 6b shows a top view of the compressive spring of FIG. 6a.

FIG. 7b shows a perspective view of the floating core of FIG. 7a.

FIG. 8b is a side view, cross-section of FIG. 8a.

FIG. 8c shows the Z-like core of FIG. 8a.

DETAILED DESCRIPTION OF THE INVENTION

Figure 1:
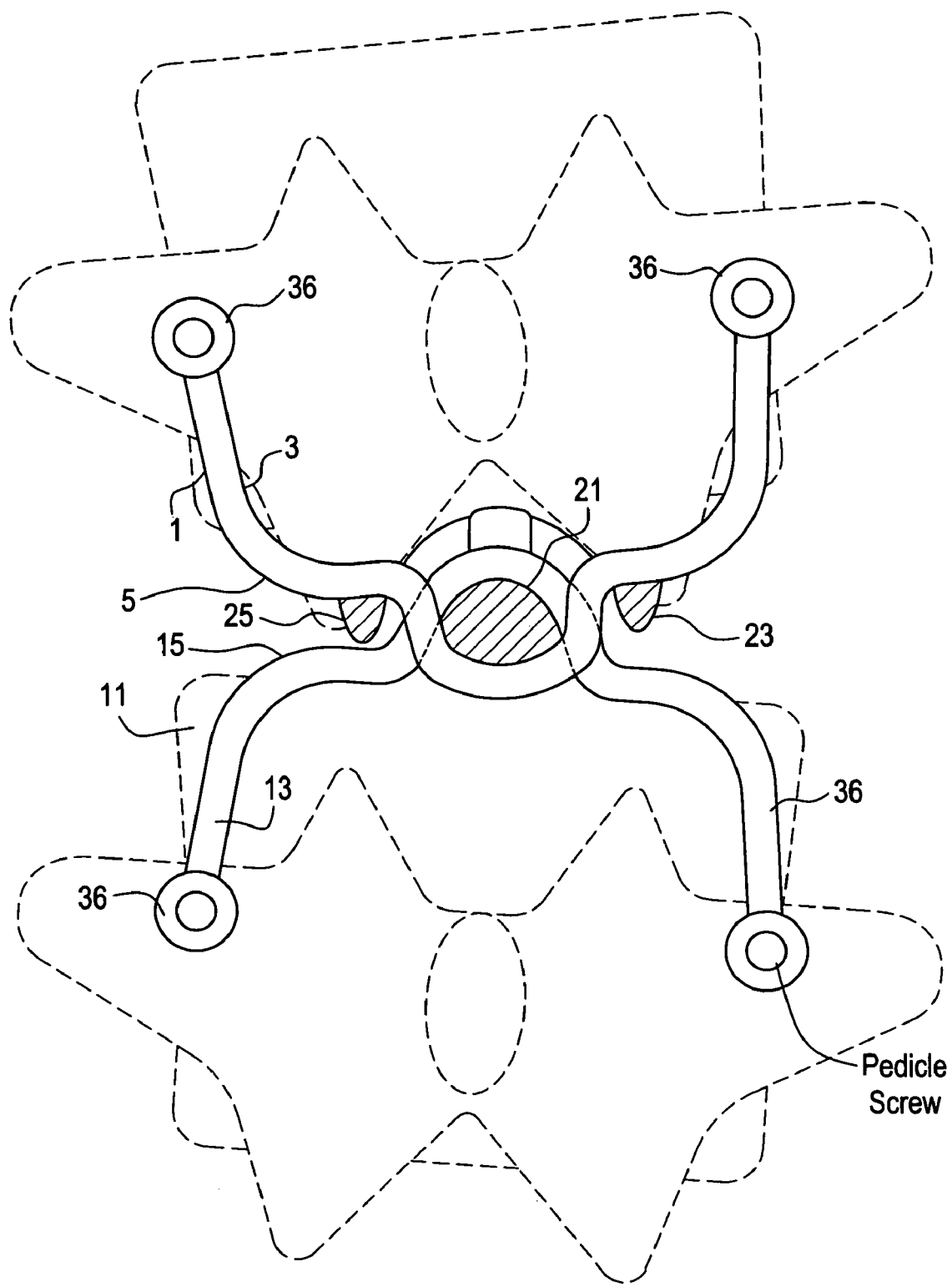
FIG. 1 is a posterior view of the present invention implanted across a functional spinal unit.

Now referring to FIG. 1, there is provided a prosthetic facet joint device comprising:
  a) a first upper component 1 adapted for fixation to a first upper vertebra comprising:

i) a first inner side 3, and ii) a second outer side 5 facing away from the first side, and b) a second lower component 11 adapted for fixation to a second lower vertebra comprising:

i) a first inner side 13, and ii) a second outer side 15 facing away from the first side, wherein the first inner side of the first upper component opposes the first inner side of the second lower component at a first central location to form a first central interface, and wherein the second outer side of the first upper component opposes the second outer side of the second lower component at a second lateral location to form a second interface, and wherein the second outer side of the first component opposes the second outer side of the second component at a third lateral location to form a third interface, and c) a first compression spring 21 associated with the first interface, d) a second compression spring 23 associated with the second interface, and e) a third compression spring 25 associated with the third interface.

Figure 2A:
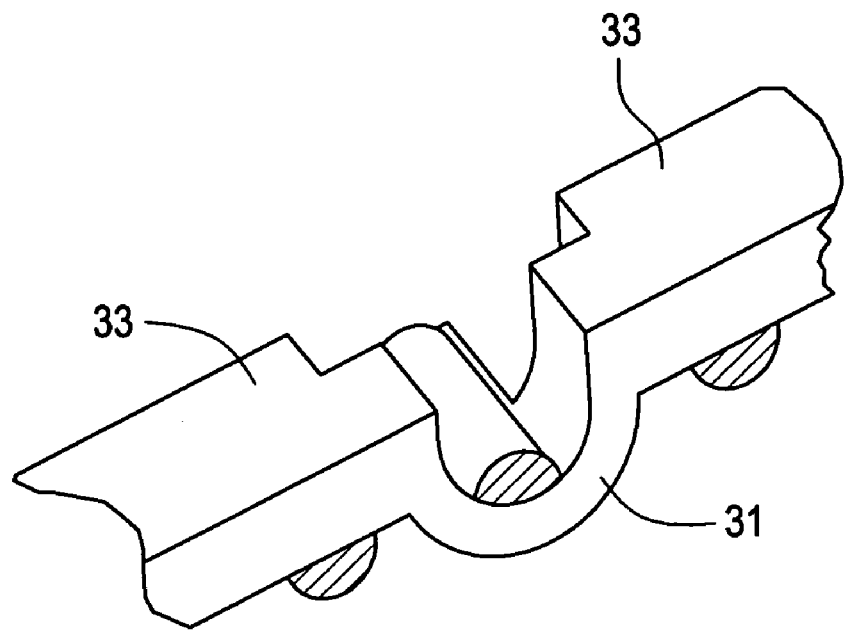
FIGS. 2a and 2b are perspective views of the central regions of the upper and lower links.
Figure 2B:
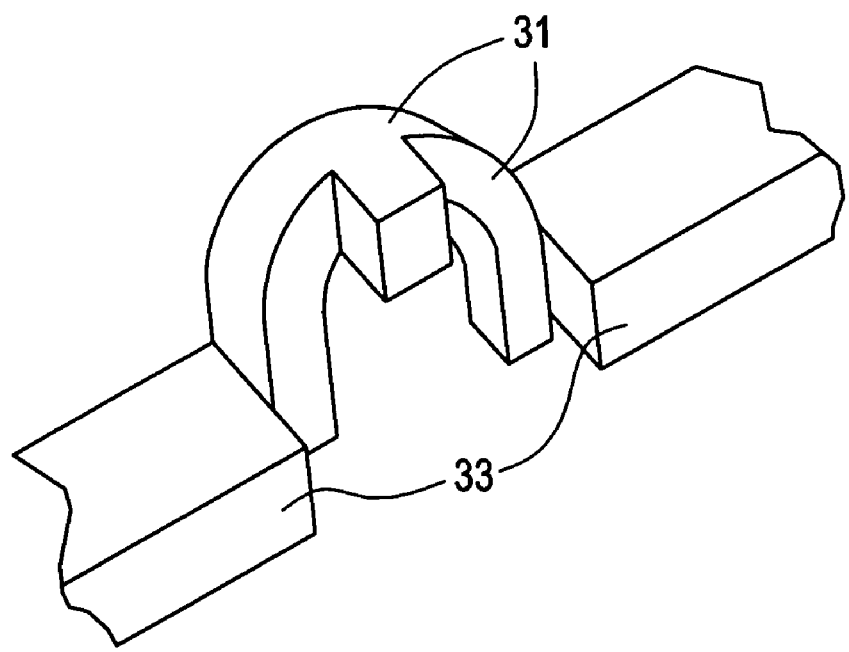
Figure 3A:
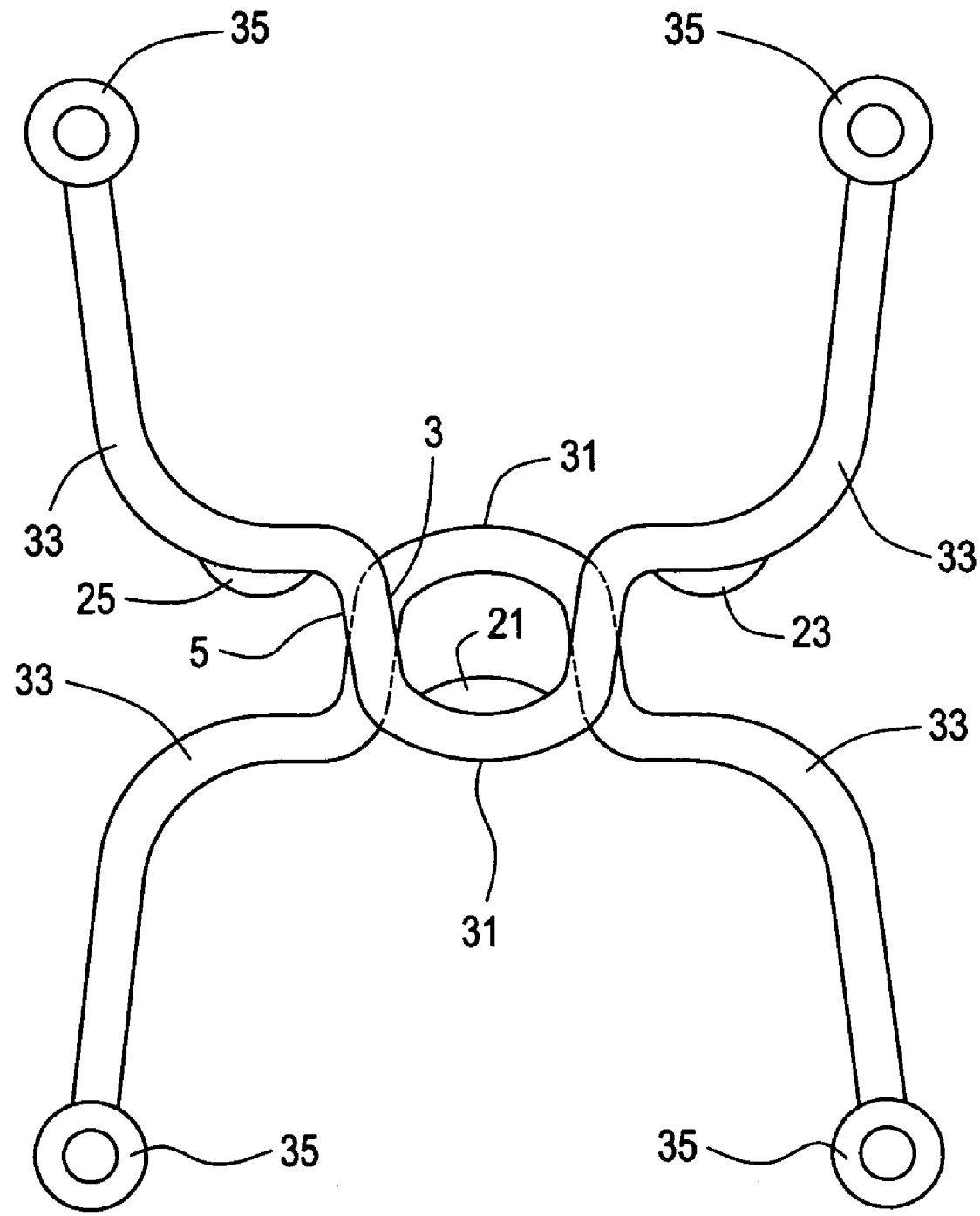
FIG. 3a shows the implant of the present invention in an unloaded position.
Figure 3B:
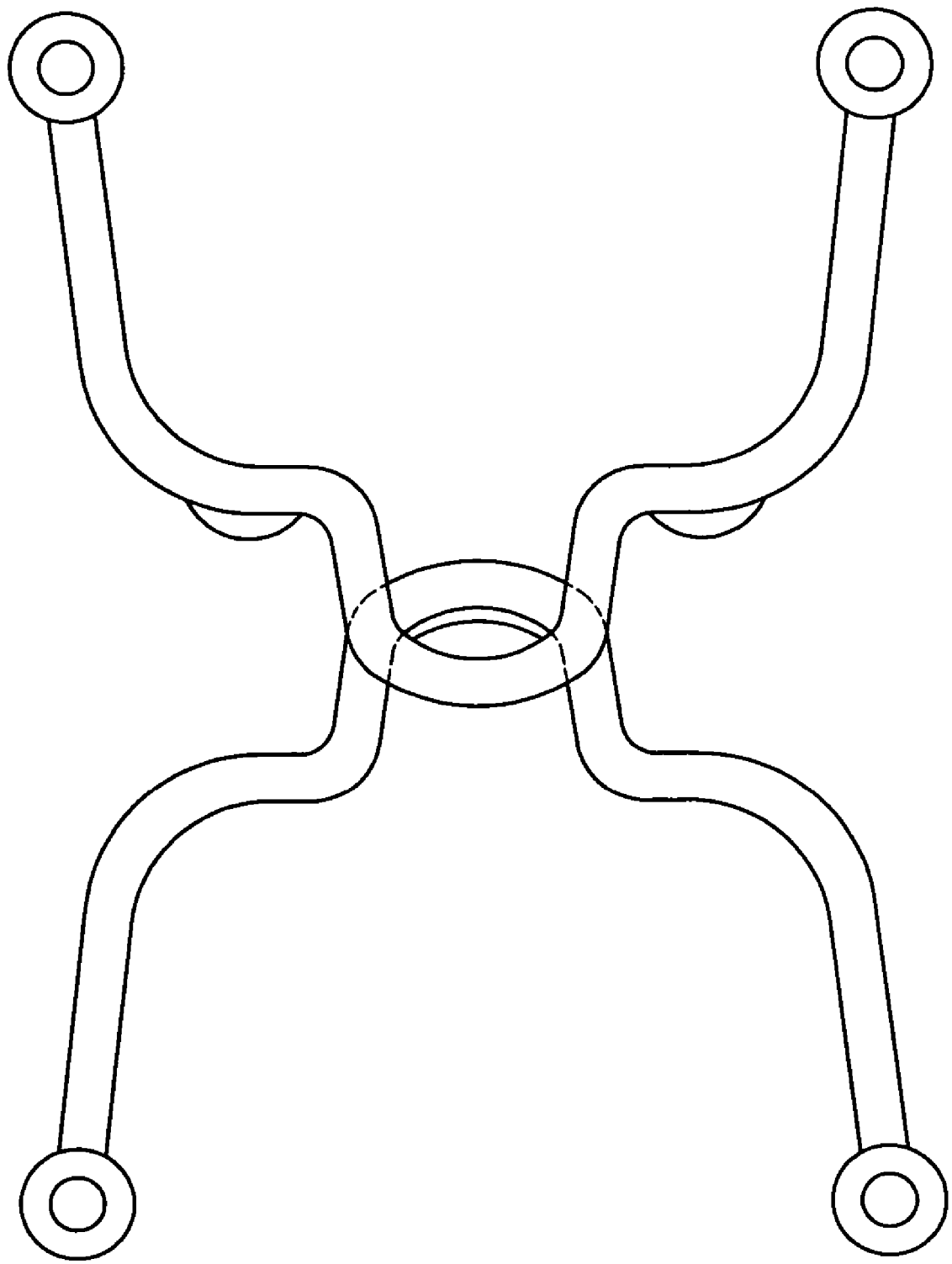
FIG. 3b shows an implant of the present invention during flexion.
Figure 3C:
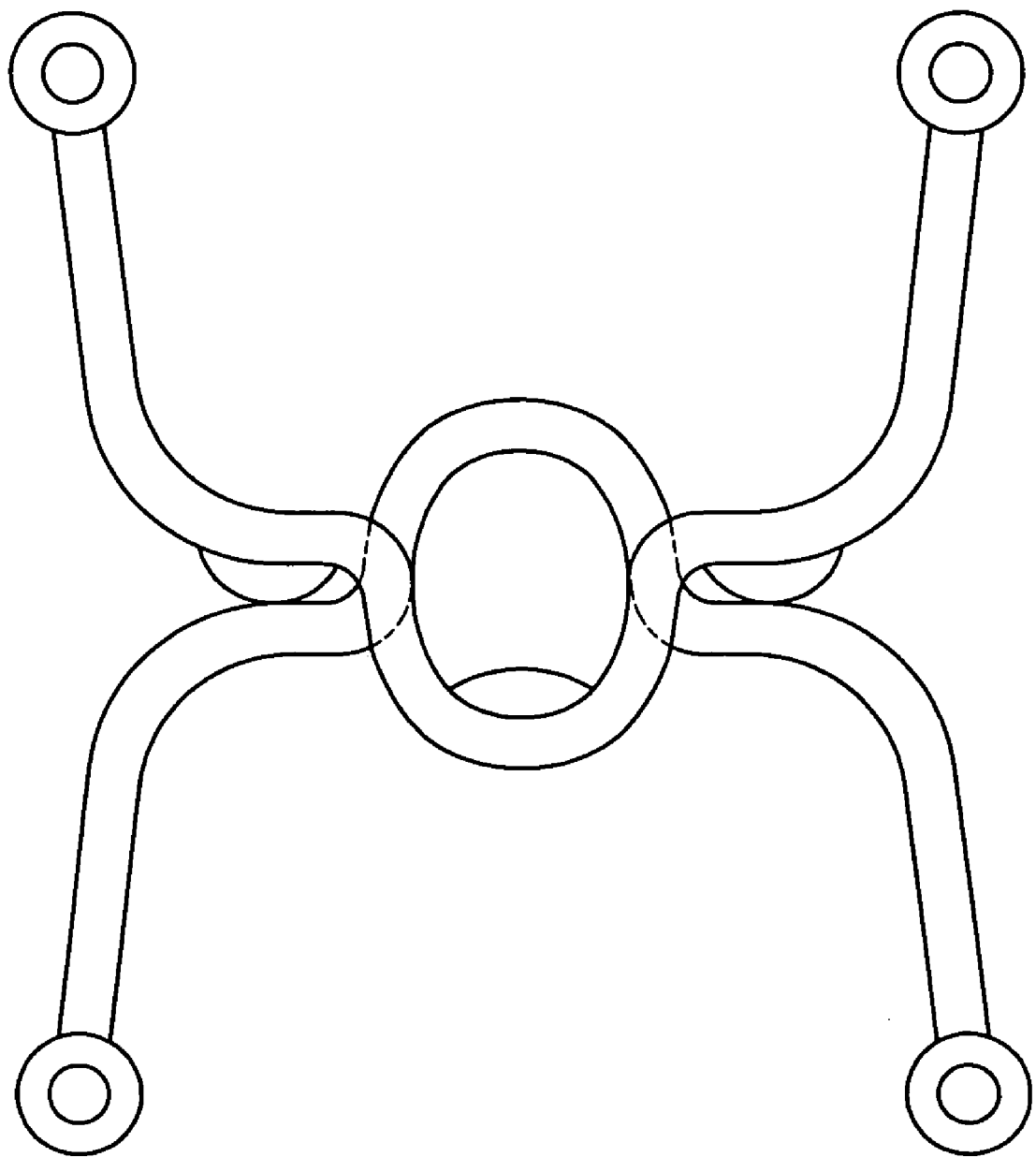
FIG. 3c shows an implant of the present invention during extension.

As shown in FIGS. 2a and 2b, preferably, each component has a general U-shape, comprising a central region 31 and lateral arms 33. In preferred embodiments, each of the first and second components has first and second lateral arms, with a distal end 35 of each arm being adapted for connection to a respective pedicle of the first and second vertebra. In preferred embodiments, the distal end of each arm is a loop adapted for receiving a pedicle screw. As shown in FIGS. 3a and 3b, the opposing arms do not touch each other in an unloaded state, and move towards each other during extension. When the associated compression resistance means begins to touch the opposing arm, it increasingly resists further movement.

The device of the present invention generally has at least two compression resistance means. However, in preferred embodiments, the device comprises three compression resistance means. Preferably, each of the first and second components has a central region, so that the first compression resistance means is attached to the central region of each at the first interface. Preferably, the second compression resistance means is attached to the first lateral arms of each component at the second interface, while the third compression resistance means is attached to the second lateral arms of each component at the third interface.

Figure 4:
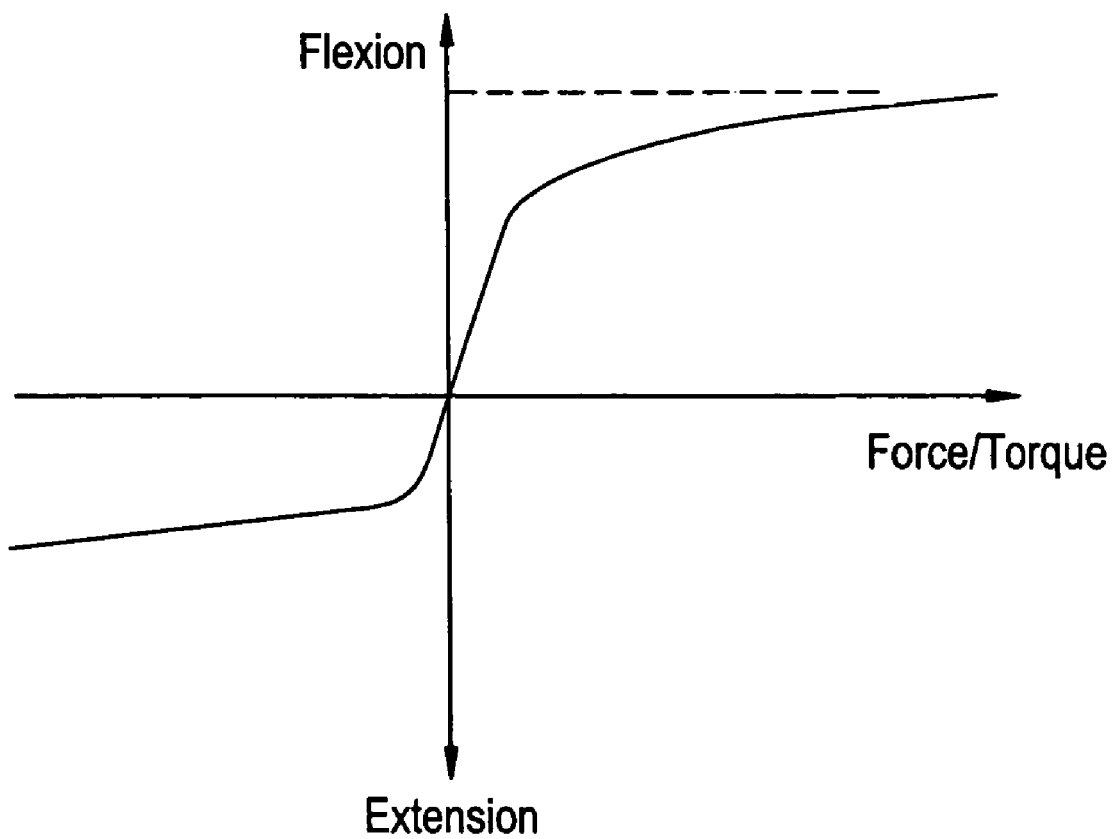
FIG. 4 is a graph showing the torque response of the implant of the present invention through flexion and extension.

As shown in FIG. 4, the selection of two lateral and one central compression resistance means provides for stiffer resistance when the lateral means are actuated (in comparison to actuation of only a single means in the central region). The result of this is that in flexion, the device is more compliant, and, in extension, the device is more stiff. This result also more fully mimics the natural response.

Any compressive element generally adapted to increasingly resist compression may be used as the compression resistance means. In some embodiments, coiled springs are used as the compression resistance means. In others, a flexible elastics material, such as rubbers, and preferably a polyurethane, is used.

Figure 5A:
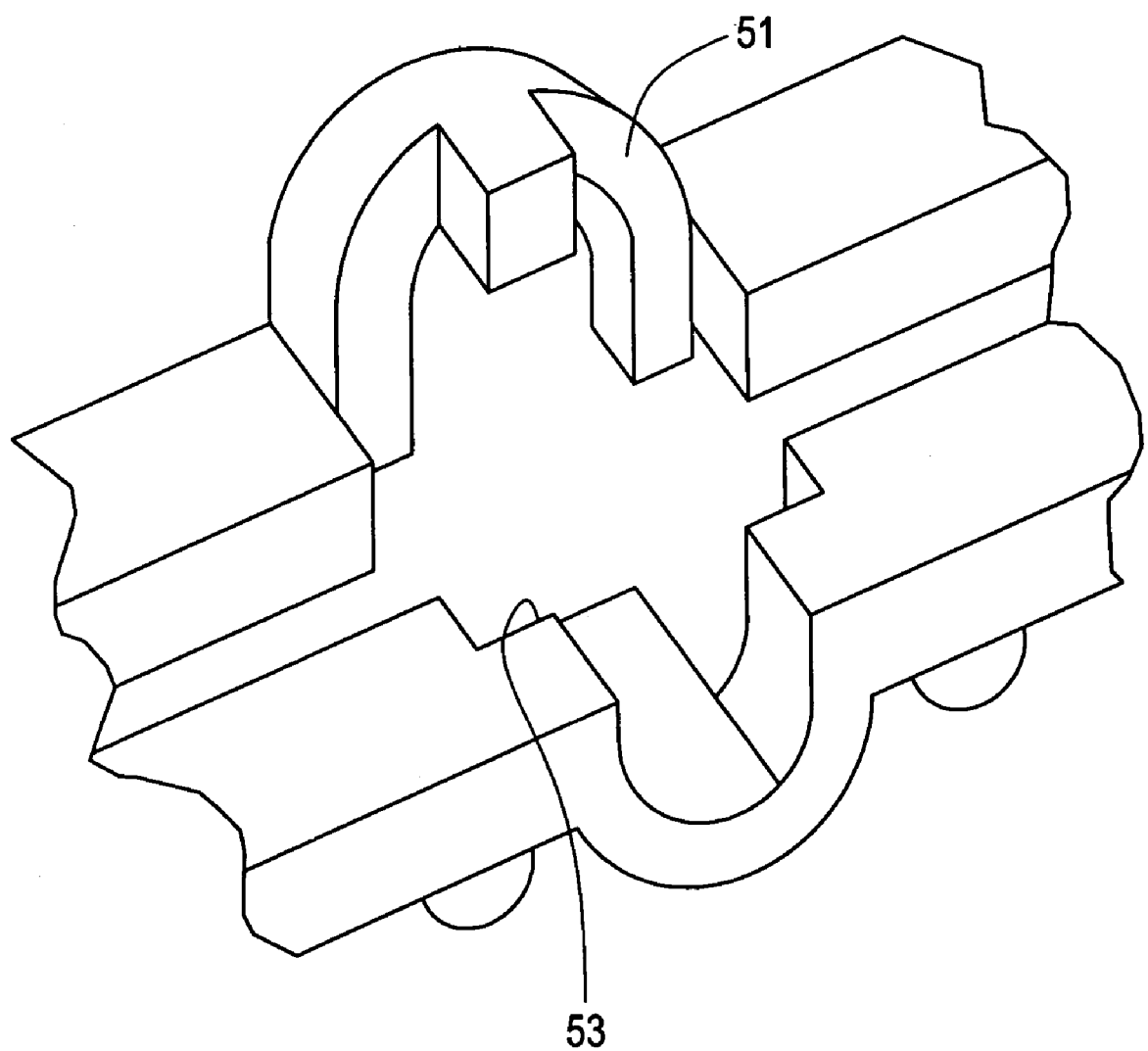
FIG. 5a shows an exploded perspective view of the implant of the present invention.
Figure 5B:
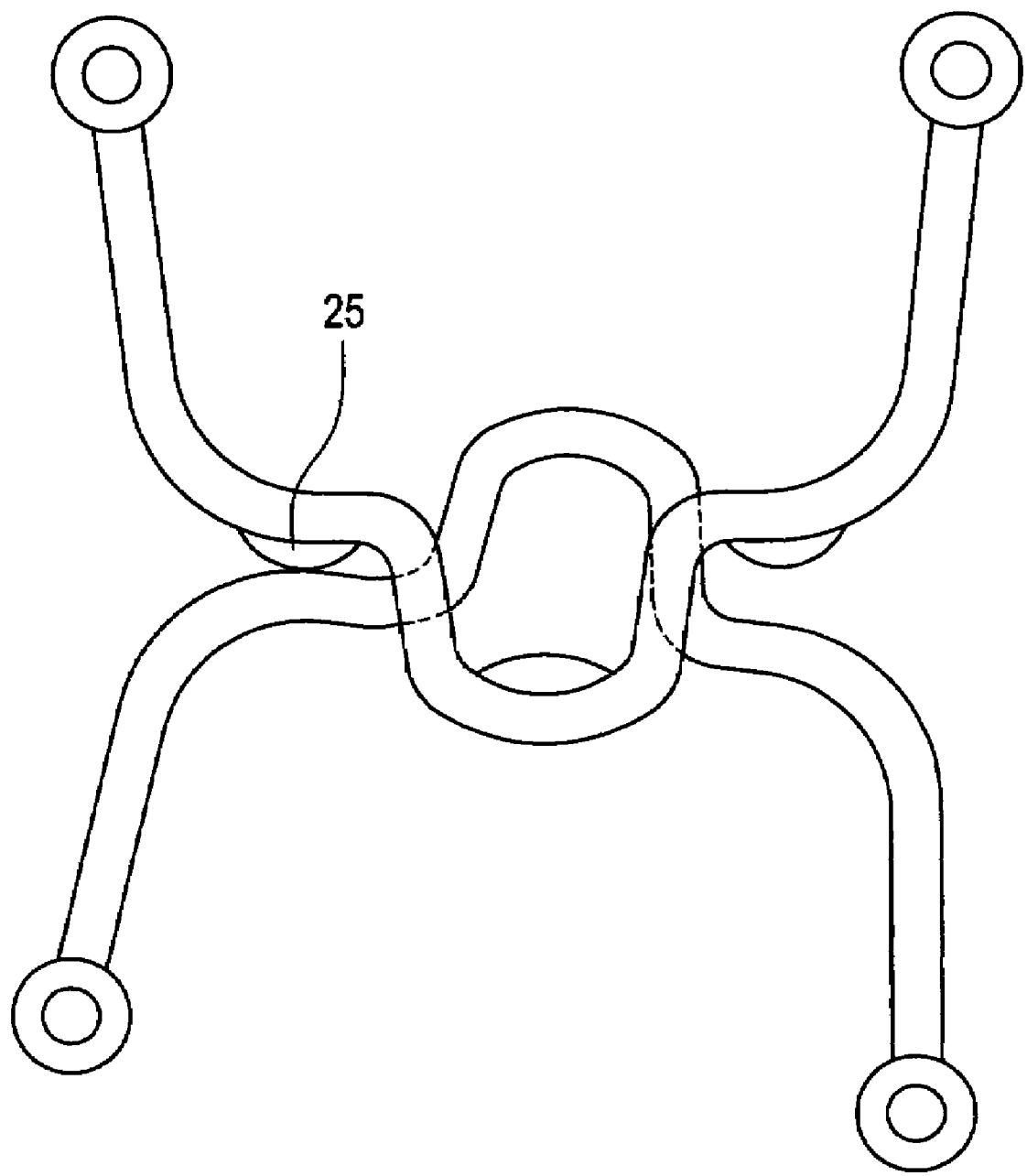
FIG. 5b shows a posterior view of the implant of the present invention in lateral bending.
Figure 5C:
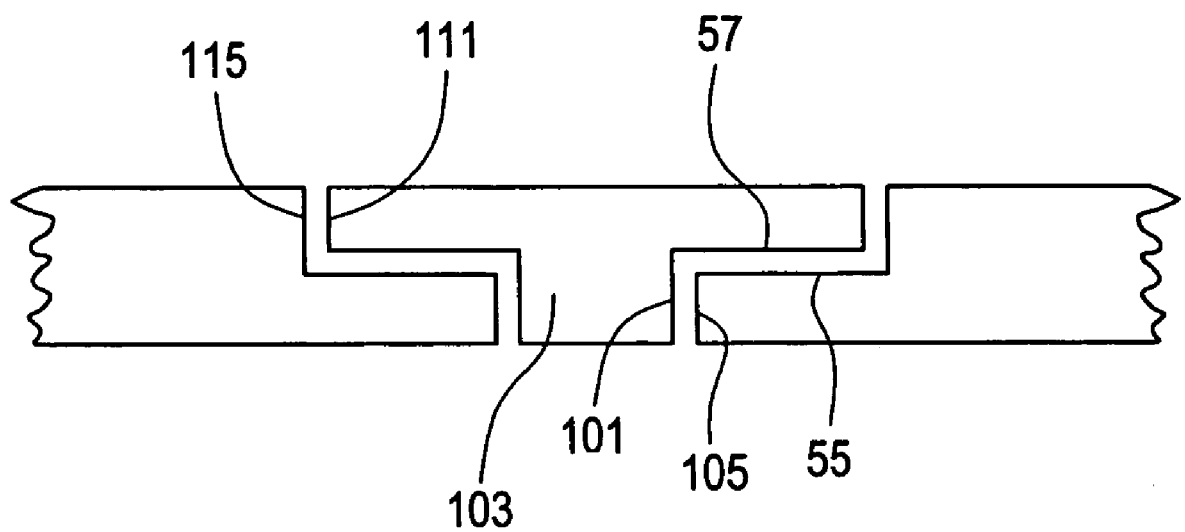
FIG. 5c shows a top view of the implant of the present invention.

FIGS. 5a-5c will now describe the reaction of the implant of the present invention to A-P shear, lateral bending and rotation.

Now referring to FIG. 5a, the central region 31 of each component is a generally U-shaped body having an inner surface 51, 53 whereby the inner surfaces 51,53 of the upper and lower components oppose each other. These opposed inner surfaces are generally polished to a high surface finish so that they become articulating surfaces that will not substantially wear when they contact each other. These opposed articulating surfaces provide a valuable function in that they prevent anterior shear of the prosthesis. Accordingly, when one of the components moves more anterior than the other, these opposing articulating surfaces 51,53 contact each other and thereby resist extreme anterior movement. Because they contact each other, these articulating surfaces may become subject to wear. Accordingly, in some embodiments (not shown), the articulating interfaces may be made of a separate, more wear resistant coating than the remainder of the component. In some embodiments, the body of the component may be metal with a polyethylene lining as the articulation surface. In some embodiments, each articulating surface is metal. In other embodiments, one surface is metal and the other is ceramic. In some embodiments, each surface is a ceramic.

In addition, the articulating surfaces need not be flat (as shown in FIGS. 2a and 2b). Rather, they may be curved.

Now referring to FIG. 5b, during lateral bending, the outer surfaces of the opposed arms on one lateral side of the prosthesis move towards each other. The prosthesis of the present invention provides arms that are slightly spaced apart, thereby allowing some lateral bending. However, upon further lateral bending, compression spring 25 contacts the opposing arm to ultimately gradually resist further being at a predetermined separation distance.

Now referring to FIG. 5c, both the lateral arms and the central region of each component contains channeled articulating surfaces that are adapted to articulate with corresponding surfaces on the other component in order to resist rotation. For example, the side surfaces 101 of the projection 103 of the central region of the upper component is adapted to articulate with the inner side surfaces 105 of the central region of the lower component. The opposing surfaces 55,57 of the central regions articulate with each other. Lastly, the outer surfaces 111 of the central region of the upper component are adapted to articulate with the inner surfaces 115 of the central region of the lower component. Because of the coordinated articulation of all of these surfaces, the implant of the present invention is adapted to resist rotation.

In some embodiments, each compression resistance means is attached to each of the opposing sides forming the associated interface. In these embodiments, the preferred compression resistance means is a coiled spring. In other embodiments, each is attached to only one side of the opposing sides forming the associated interface. In these embodiments, the preferred compression resistance means is a rubber material.

In preferred embodiments, the lateral arms of each of the first and second components the each respective component a concave profile. This concave profile generally defines a first, relatively large radius. In preferred embodiments, the central region of each component forms a second concave profile having a second, somewhat smaller radius.

Preferably, the central region of each component also has a general U-shape, defining an apex. The inner surfaces of the central regions move towards each other during compression, with the associated compression resistance means resisting further movement less than a predetermined separation distance. The central regions are of the two components are located so that one central region is closer to the vertebrae than the other central region, and so that the posterior face of the central region closer to the vertebra opposes the anterior face of the central region further from the vetebra. In this manner, these opposing faces can articulate with one another and resist anterior-posterior shear.

In some embodiments, the central region of each further comprises an extension extending laterally from the apex. The extensions of the two central regions preferably extend laterally in opposite directions and provide opposing upper and lower faces, so that these opposed faces can articulate with one another to prevent rotation.

Figure 6A:
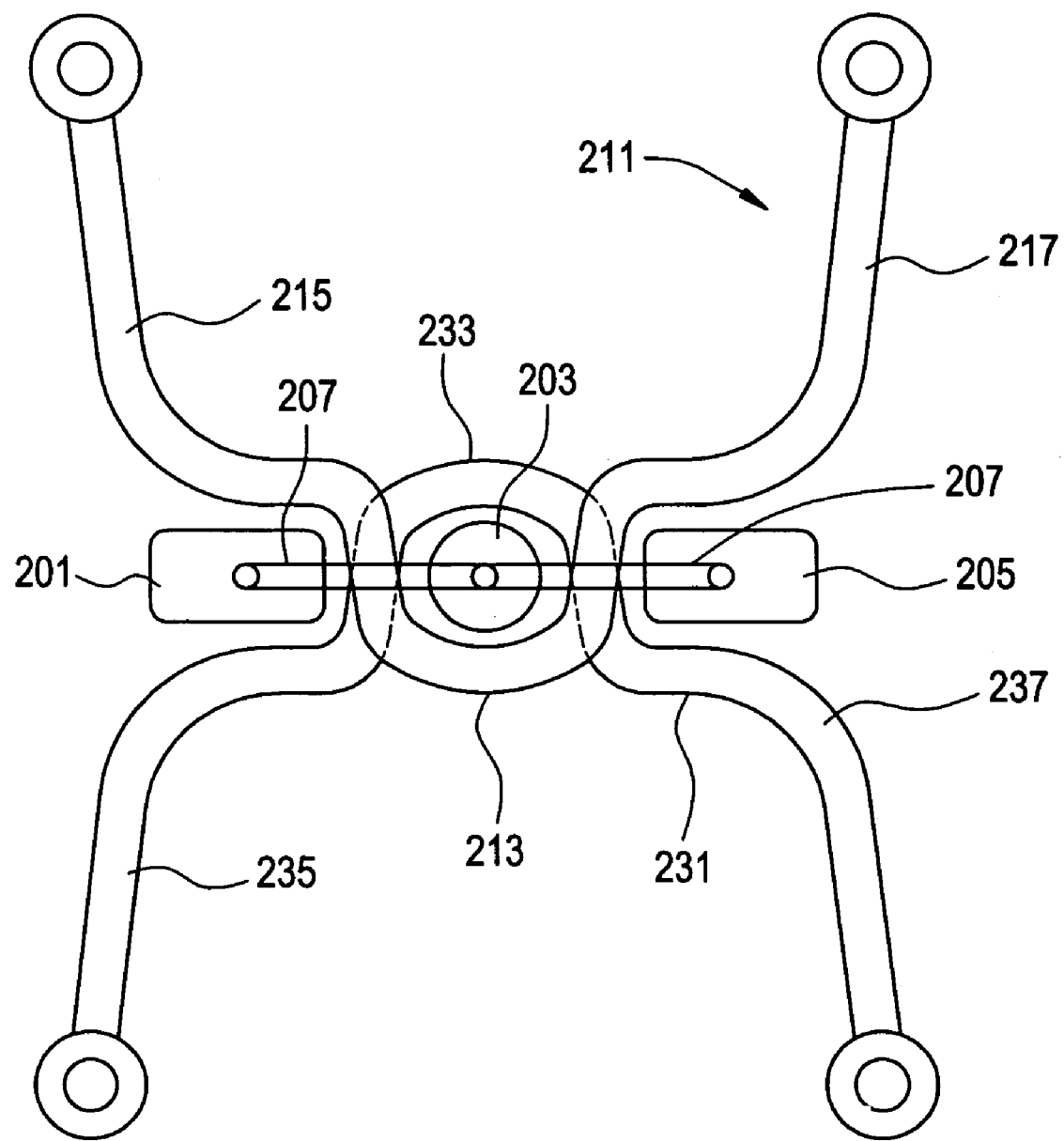
FIG. 6a shows an implant of the present invention having a floating compressive spring.

In still other embodiments, each compression resistance means is adapted to float between the opposing sides that form its associated interface. Now referring to FIG. 6a, there is provided an implant of the present invention having floating compression springs 201, 203, 205 disposed between the respective lateral arms and central projections of the implant. These implants are not attached to the upper or lower components, but rather are attached to each other by means of a cable 207.

Therefore, in accordance with the present invention, there is provided: a prosthetic facet joint device comprising:
a) a first component 211 adapted for fixation to a first vertebra comprising:
    i) a first U-shaped central region 213, and
    ii) a first 215 and second 217 lateral arms extend laterally from the first central region, and
b) a second component 231 adapted for fixation to a second vertebra comprising:
    i) a second U-shaped central region 233, and
    ii) a first 235 and second 237 lateral arms extend laterally from the second central region, and
wherein the first lateral arm of the first component opposes the first lateral arm of the second component at a first location,
wherein the second lateral arm of the first component opposes the second lateral arm of the second component at a second location, and wherein the first and second U-shaped regions opposed each other at a third location,
    c) a first compression resistance means 201 freely interposed between the first lateral arms at the first location, and
    d) a second compression resistance means 203 freely interposed between the second lateral arms at the second location, and
    e) a third compression resistance means 205 freely interposed between the central regions at the third location.

Figure 6B:
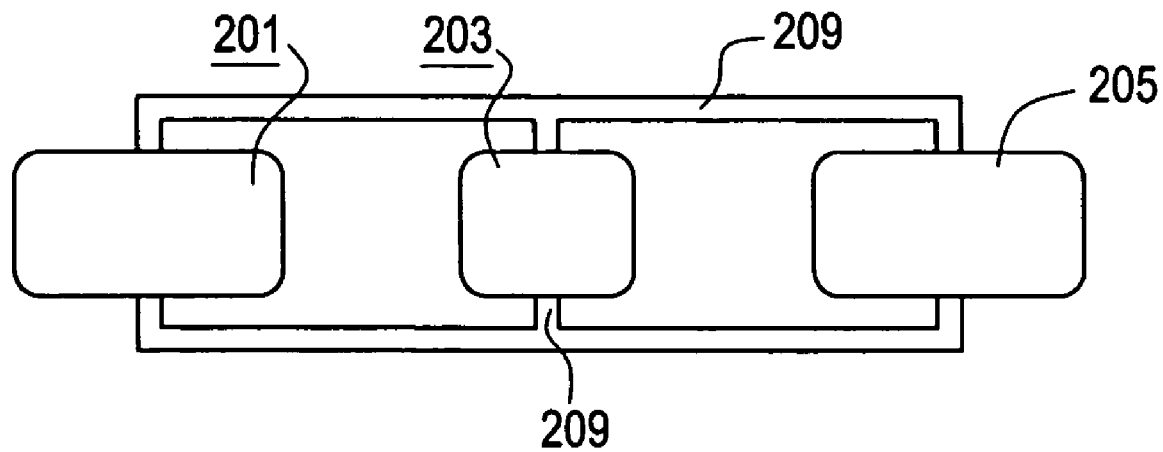

Now referring to FIG. 6b, in some floating core embodiments, the compression springs are attached to each other by a plurality of cable portions 209.

Figure 7A:
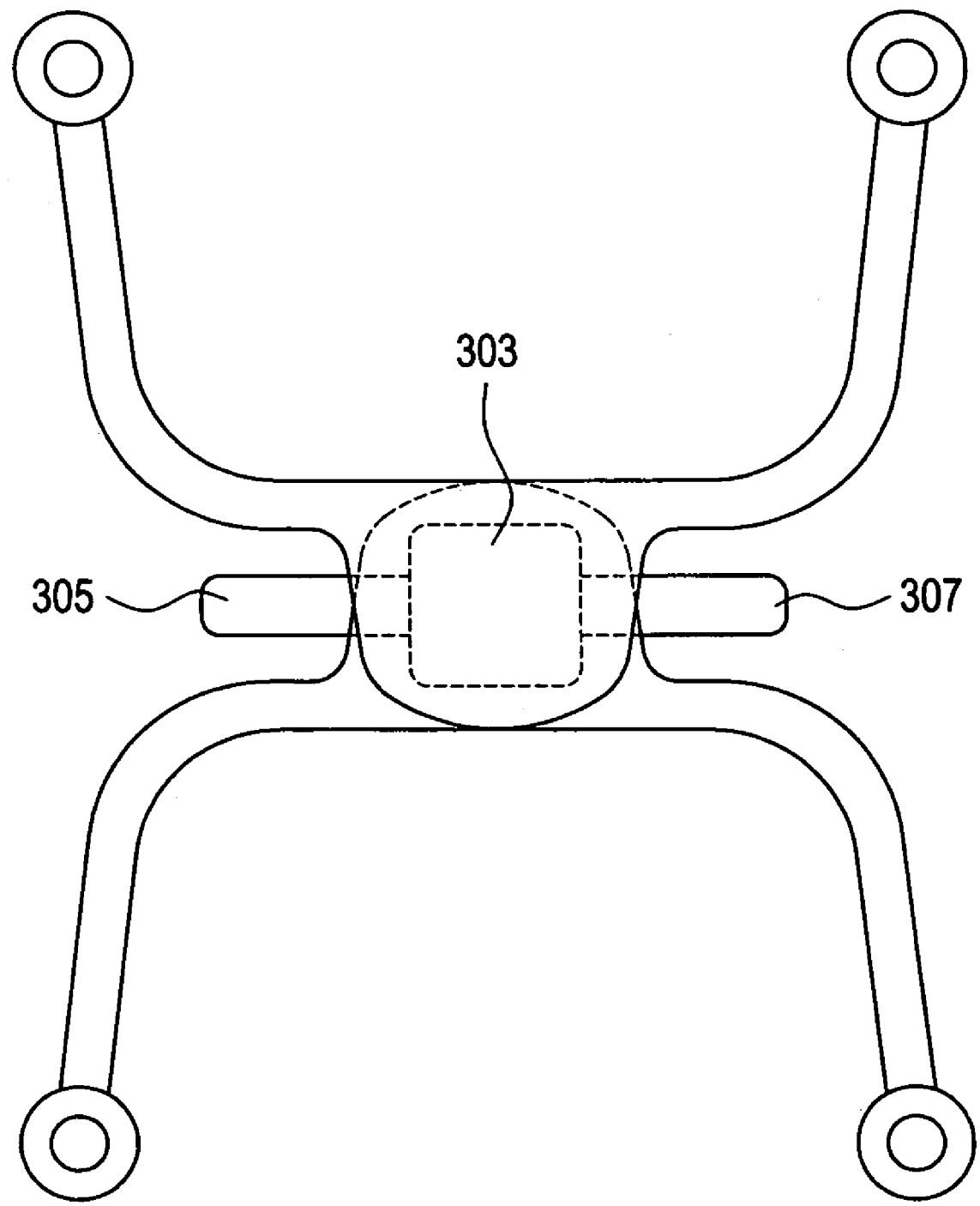
FIG. 7a shows an implant of the present invention having a floating core.
Figure 7B:
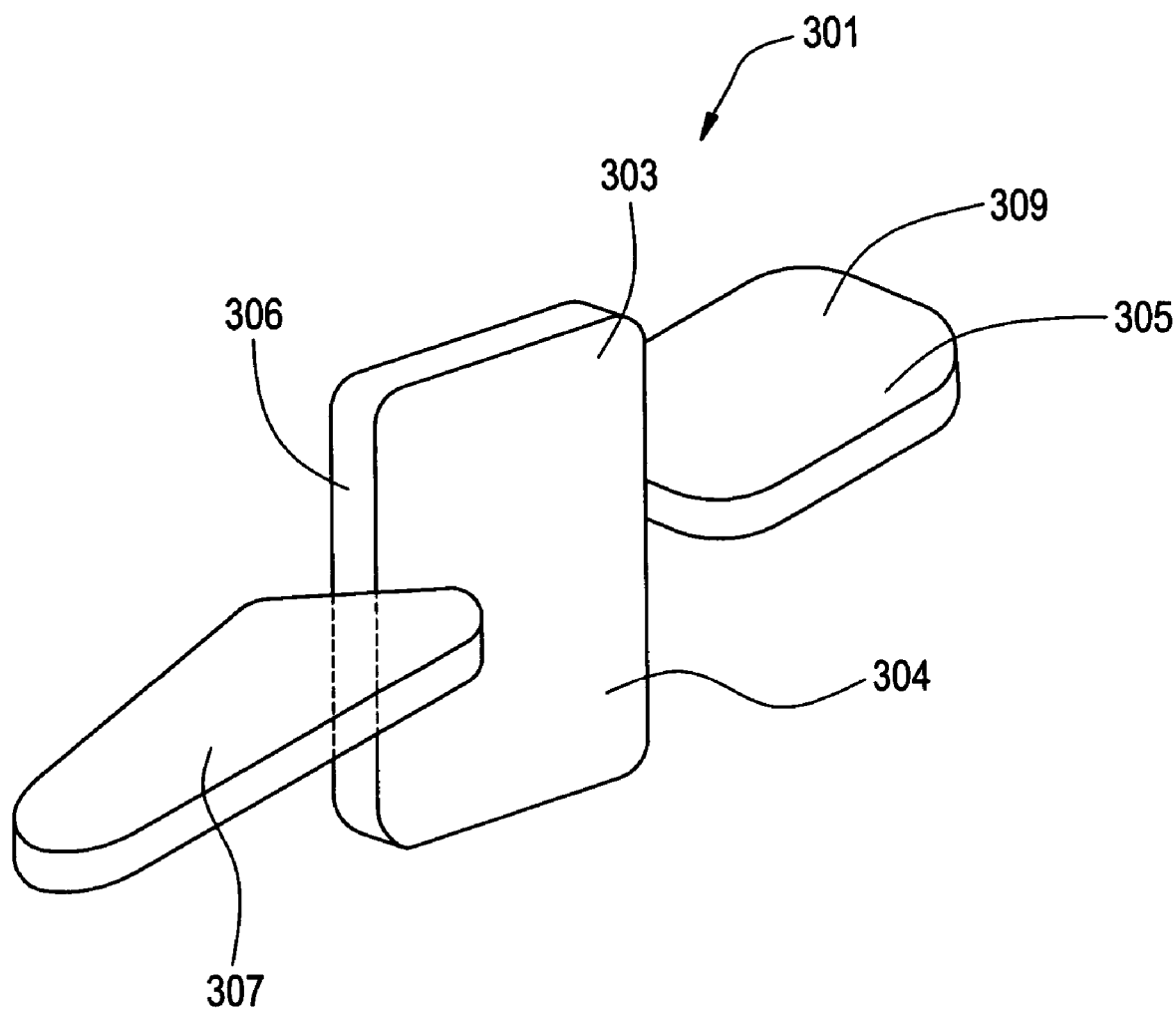

Now referring to FIG. 7a-c, there is provided a floating compression spring 301 of the present invention adapted to float freely between the upper and lower components and provide compression resistance in both the central and lateral regions of the implant. The floating compression spring comprises a central cushion 303 that is elongated vertically and is adapted to be interposed between the articulating surfaces of the opposed central regions. The front 304 and back (not shown) surfaces of the central cushion are adapted to articulate with the articulating surfaces of the opposed central regions of the upper and lower component and so are made of polished UHMWPE. Extending lateral from the central cushion are lateral cushions 305, 307 that are adapted to fit between the opposed surfaces of lateral arms disposed on each side of the implant. The upper 309 and lower (not shown) surfaces of these lateral cushions are also adapted for articulation and are preferably made of UHMWPE.

Therefore, in accordance with the present invention, there is provided a prosthetic facet joint device comprising:

a) a first component adapted for fixation to a first vertebra comprising:
    i) a first U-shaped central region, and
    ii) a first and second lateral arms extend laterally from the first central region, and
b) a second component adapted for fixation to a second vertebra comprising:
    i) a second U-shaped central region, and
    ii) a first and second lateral arms extend laterally from the second central region, and
c) a floating core having
    i) a central cushion 303 having a front surface 304, a back surface and side surfaces 306 surfaces, and
    ii) lateral cushions 305,307 extending from each side surface.

wherein the first lateral arm of the first component opposes the first lateral arm of the second component at a first location, wherein the second lateral arm of the first component opposes the second lateral arm of the second component at a second location, and wherein the first and second U-shaped regions opposed each other at a third location, wherein the central cushion occupies the third location, and the lateral cusion occupies the first and second locations.

Figure 8A:
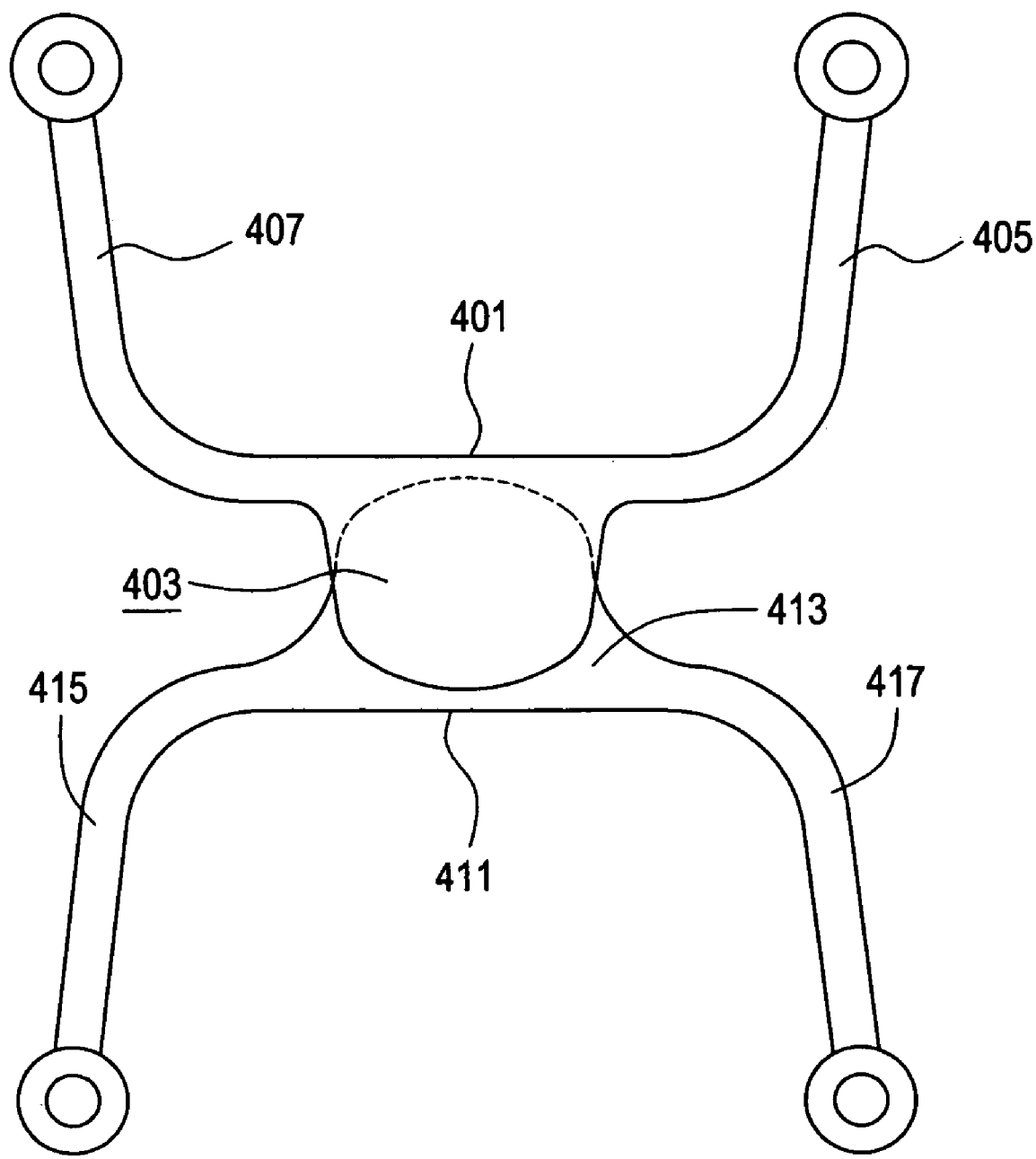
FIG. 8a shows an implant of the present invention having a Z-like core.
Figure 8B:
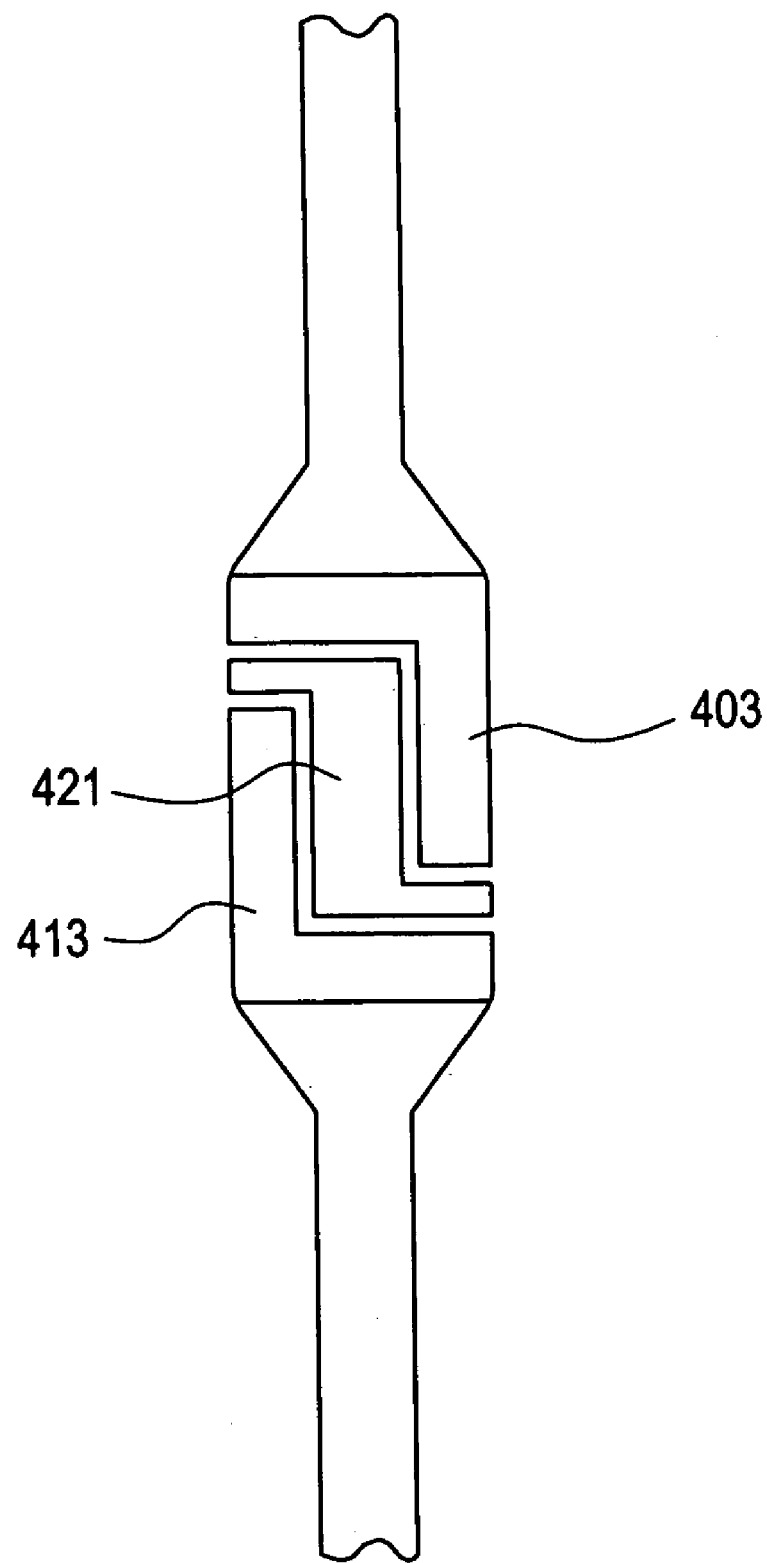
Figure 8C:
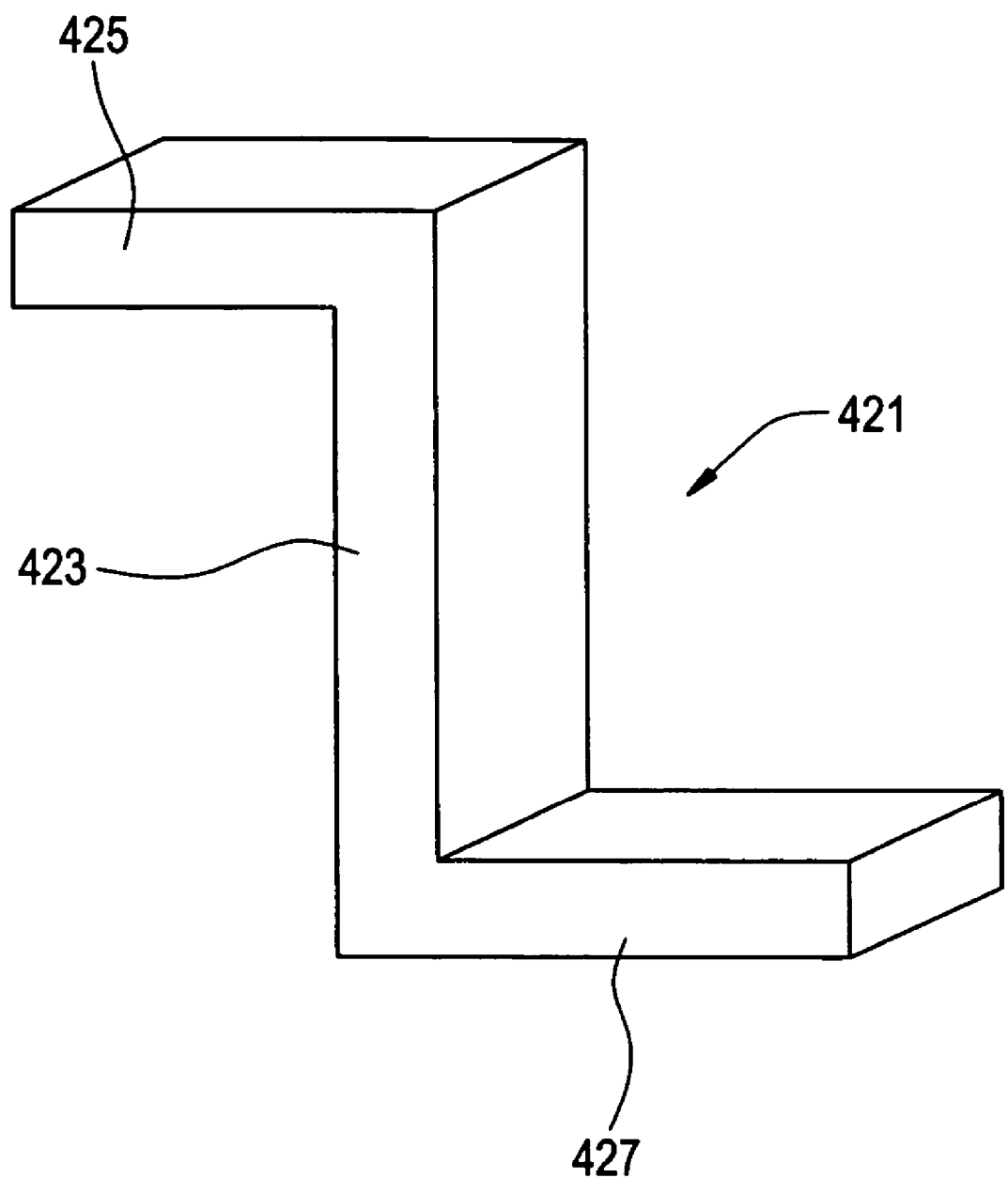

Now referring to FIG. 8 a-d, there is provided a floating core 421 having a Z-like configuration. This Z-like core is adapted to fit within the Z-like space formed between opposed L-shaped central regions of the upper and lower components. The Z-shaped core comprised a middle shank section 423 and first 425 and second 427 extensions stops extending in opposite directions from either end of the middle shank section.

Therefore, in accordance with the present invention, there is provided: a prosthetic facet joint device comprising:
a) a first component 401 adapted for fixation to a first vertebra comprising:
    i) a first L-shaped central region 403, and
    ii) a first 405 and second 407 lateral arms extend laterally from the first central region, and
b) a second component 411 adapted for fixation to a second vertebra comprising:
    i) a second L-shaped central region 413, and
    ii) a first 415 and second 417 lateral arms extend laterally from the second central region, and
c) a Z-shaped core 421 comprising
    i) a middle shank section 423 and
    ii) first 425 and second 427 extensions stops extending in opposite directions from either end of the middle shank section.

wherein the first and second L-shaped regions oppose each other at a third location to form a Z-shaped space, and wherein the Z-shaped core occupies the Z-shaped space.

I claim:
1. A prosthetic facet joint device comprising:
    a) a first component adapted for fixation to a first vertebra comprising:
        i) a first side, and
        ii) a second side facing away from the first side,
        iii) a first central region, and
        iv) first and second lateral arms extend laterally from the first central region, and
    b) a second component adapted for fixation to a second vertebra comprising:
        i) a first side, and ii) a second side facing away from the first side,
iii) a first central region, and
iv) first and second lateral arms extend laterally from the first central region, and wherein the first side of the first component opposes the first side of the second component at a first location to form a first interface, and wherein the second side of the first component opposes the second side of the second component at a second location to form a second interface, wherein the second side of the first component opposes the second side of the second component at a third location to form a third interface, and c) a first compression resistance means associated with the first interface, and
d) a second compression resistance means associated with the second interface, and
e) a third compression resistance means associated with the third interface, wherein the lateral arms of the first component form a concave profile having a first radius, wherein the central region of the first component forms a concave profile having a second radius, wherein the second radius is smaller than the first radius, wherein the central region has a general U-shape having an apex, and wherein central region further comprises an extension extending laterally from the apex.

2. The device of claim 1 wherein the first component has first and second lateral arms, each arm being adapted for connection to a pedicle of the first vertebra.

3. The device of claim 2 wherein the first component has a central region, wherein the first compression resistance means is attached to the central region at the first interface.

4. The device of claim 2 wherein the second compression resistance means is attached to the first lateral arm at the second interface.

5. The device of claim 1 wherein the third compression resistance means is attached to the second lateral arm at the third interface.

6. The device of claim 1 wherein the first compression resistance means is attached to only one of the first side of the first component and the first side of the second component.

7. The device of claim 1 wherein the second component has a central region, wherein the first compression resistance means is attached to the central region of the second component at the first interface.

8. The device of claim 1 wherein the second compression resistance means is attached to the first lateral arm of the second component the second interface.

9. The device of claim 1 wherein the third compression resistance means is attached to the second lateral arm of the second component at the third interface.

* * * * *

UNITED STATES PATENT AND TRADEMARK OFFICE
CERTIFICATE OF CORRECTION

PATENT NO. : 7,655,044 B2 Page 1 of 1
APPLICATION NO. : 11/011330
DATED : February 2, 2010
INVENTOR(S) : Seungkyu Daniel Kwak It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1254 days.

Signed and Sealed this

Twenty-third Day of November, 2010

David J. Kappos
*Director of the United States Patent and Trademark Office*